(12) United States Patent
Ferrone et al.

(10) Patent No.: US 7,348,153 B2
(45) Date of Patent: Mar. 25, 2008

(54) METHOD FOR IDENTIFYING AND DESIGNING IMMUNOGENIC PEPTIDES

(75) Inventors: Soldano Ferrone, Buffalo, NY (US); Constantin Ioannides, Houston, TX (US); James L. Murray, Houston, TX (US); Kouichiro Kawano, Kurume (JP)

(73) Assignees: Health Research, Inc., Buffalo, NY (US); Board of Regents, The University of Texas Systems, Austin, TX (US)

( * ) Notice: Subject to any disclaimer, the term of this patent is extended or adjusted under 35 U.S.C. 154(b) by 0 days.

(21) Appl. No.: 11/286,917

(22) Filed: Nov. 23, 2005

(65) Prior Publication Data

US 2006/0141532 A1  Jun. 29, 2006

Related U.S. Application Data

(60) Provisional application No. 60/630,718, filed on Nov. 24, 2004.

(51) Int. Cl.
*G01N 33/53* (2006.01)
(52) U.S. Cl. ..................................... 435/7.1
(58) Field of Classification Search .................. 435/7.1
See application file for complete search history.

(56) References Cited

U.S. PATENT DOCUMENTS 6,949,244 B1 * 9/2005 Chatterjee et al. ....... 424/131.1
7,090,842 B1 * 8/2006 Chatterjee et al. ....... 424/131.1
2004/0037840 A1 * 2/2004 Beier et al. .............. 424/185.1

OTHER PUBLICATIONS

Tahara et al. Clin Cancer Res. Aug. 1999;5(8):2236-2241).*
Schirle et al. (J. Immunol. Methods. 2001; 257: 1-16).*
Anderson et al. (Tissue Antigens. Jun. 2000; 55 (6): 519-531).*
Feltkamp et al. (Mol. Immunol. Dec. 1994; 31 (18): 1391-1401).*
Ezzell (J. NIH Res, 1995, 7:46-49).*
Burgess et al, Journal of Cell Biology vol. 111 Nov. 1990 2129-2138.*
Lazar et al Molecular and Cellular Biology Mar. 1988 vol. 8 No. 3 1247-1252).*
Schwartz et al, Proc Natl Acad Sci USA vol. 84:6408-6411 (1987).*
Lin et al Biochemistry USA vol. 14:1559-1563 (1975).*
Murray et al. Cancer Res. 64:5481-5488 (Aug. 1, 2004).*
Tahara et al. Clin. Cancer Res. 5:2236-2241 (1999).*
Sequence search output for SEQ ID No. 24 (pp. 1-5).*

* cited by examiner

*Primary Examiner*—Larry R. Helms
*Assistant Examiner*—Lynn Bristol
(74) *Attorney, Agent, or Firm*—Hodgson Russ LLP

(57) ABSTRACT

The invention provides a method for identifying peptides for use in increasing a cytotoxic T lymphocytes (CTL) response to an antigen. The method comprises the steps of comparing the amino acid sequence of the VH and/or VL portions of an anti-idiotypic monoclonal antibody to the amino acid sequence of an antigen to identify regions of homology between the Ab2 and the antigen, and to further identify an HLA binding motif in a homologous region. The identified homologous region which comprises an HLA binding motif defines a peptide sequence that is useful for stimulating a CTL response. Also provided are peptides identified by the method, and a method of using the peptides to stimulate a CTL response in an individual.

3 Claims, 6 Drawing Sheets

Figure 2

V_H
```
                                    10                                    20
AAG ATG CTT CTG GTT TTG CTG TAC TCC AAG CTT TCT TCC CAG TGC GCT GAA GAT CAG ACT GCT
 K   M   L   L   V   L   L   Y   S   K   L   S   S   Q   C   A   E   D   Q   T   A

GTG CAC CTA CAG AGC CTG TCC ATC ACA TGC ACT GTC TCT GGT TCG CAT (35A-B) TAT CCA GAT
 V   H   L   Q   S   L   S   I   T   C   T   V   S   G   S   H           Y   P   D
            40                                              CDR1                 60

ATA ATG TAC ACT GGG TTC - GCC AAG CCT CCA GGA AAG - GGT CTG GAG TGG CTG GGA ATG ATA
 I   M   Y   T   G   F     A   K   P   P   G   K     G   L   E   W   L   G   M   I
                                                                                 80

TGG  GGT GCT GGA AGT ACA GAC TAT AAT TCA GCT CTC AAA TCC AGA CTC ACC ATC AAC AAG GAC
 W    G   A   G   S   T   D   Y   N   S   A   L   K   S   R   L   T   I   N   K   D
                          CDR2
                                              90

AAC TCC AAG AGC (82A-C) CAA GTT TTC TTA AAA ATG AAC AGT CTG CAA ATT GAT GAC ACA GCC
 N   S   K   S         Q   V   F   L   K   M   N   S   L   Q   I   D   D   T   A
100                                                                              110

ATG  TAC TAC TGT GCC AGA GAG AGA CAT GGT AAC CCG TTT (100A-L) GCT TAC-------TGG
 M    Y   Y   C   A   R   E   R   H   G   N   P   F             A   Y         W
                       120                      124 CDR3

GGC CAA GGG ACT CTG GTC ACT GTC TCT GCA GCC AAA
 G   Q   G   T   L   V   T   V   S   A   A   K
```

V_L
```
                                    10                                    20
----- AAA CCA TGC CCT GTA GCT AGT ATG TCG ATC ACC TTG CTG CTA GCA GCA CAC TCT GAG CAG CTA
       K   P   C   P   V   A   S   M   S   I   T   L   L   L   A   A   H   S   E   Q   L
                             30                                      40

AGT TAT (27A)-ATA TGT AAG CTG TAC— CAC AGA ACA GAC AGC ACC AAC TCC TAT CTA TGC TGC
 S   Y           I   C   K   L   Y   H   R   T   D   S   T   N   S   Y   L   C   C
50                CDR1                   60                                       70

GTC CAA TCT AGA ATC TGG--ATC CCA GCC AGG TTT AGT GGC AGT GGG TCT GGG ACA GAC TTC ACC CTC
 V   Q   S   R   I   W   I   P   A   R   F   S   G   S   G   S   G   T   D   F   T   L
               CDR2                  80                                             90

AAC ATC CAT CCT GTG GAG GAG GAG GAT GCT GCA ACC TAT TAC TGT CAG CAA AGT AAT GAG GAT CCG
 N   I   H   P   V   E   E   E   D   A   A   T   Y   Y   C   Q   Q   S   N   E   D   P
                                                                 CDR3

TAC ACG TTC GGA GGG GGG (95A-F) ACC AAG CTG GAA ATA AAA CGG GCT GAT GCT GCA CCA (106A) ACT
 Y   T   F   G   G   G           T   K   L   E   I   K   R   A   D   A   A   P           T
                          100                                                         107
```

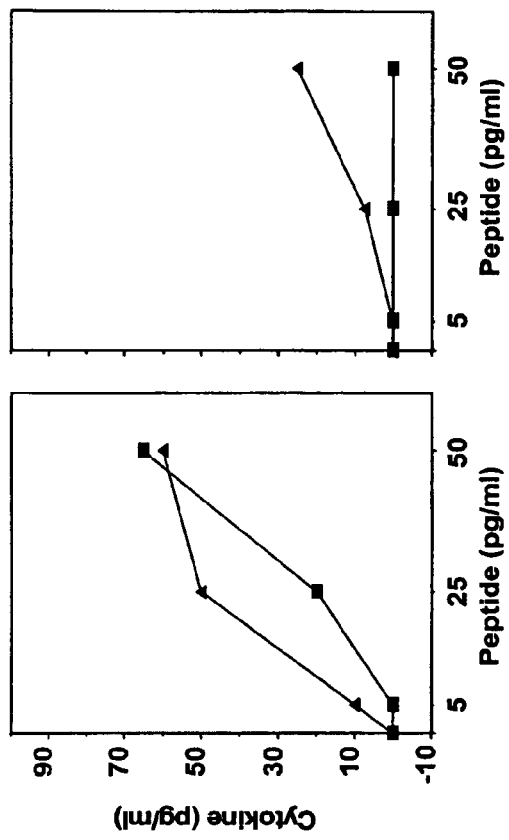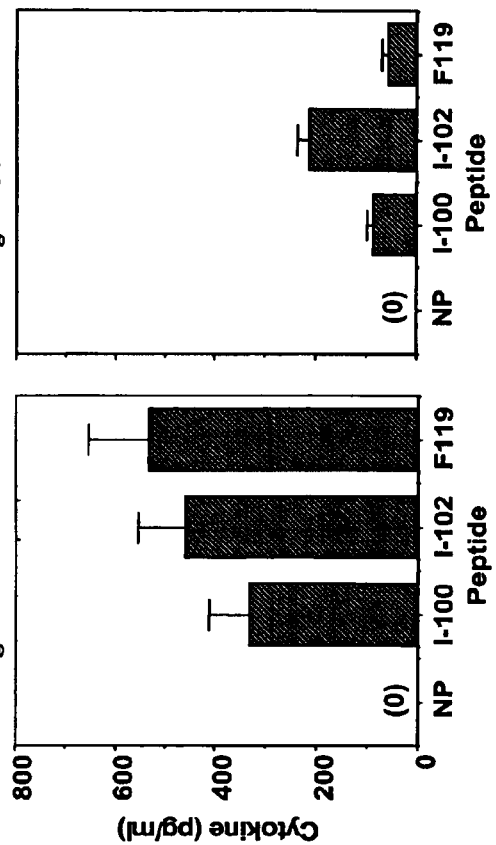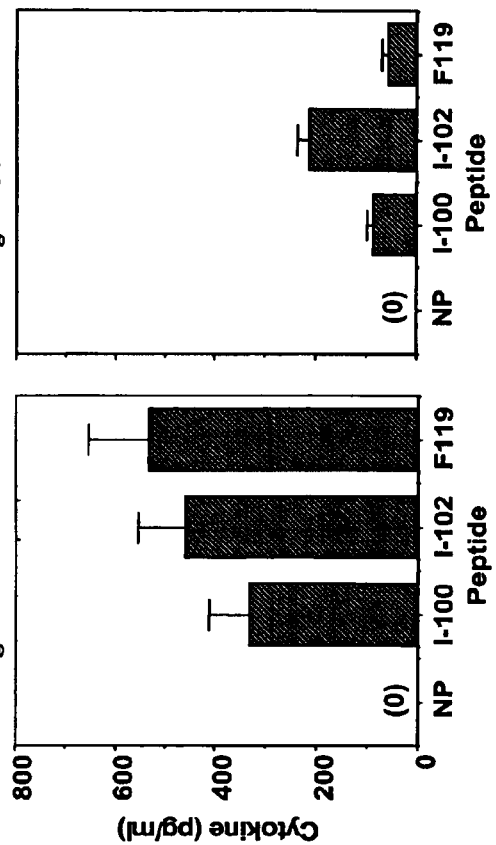

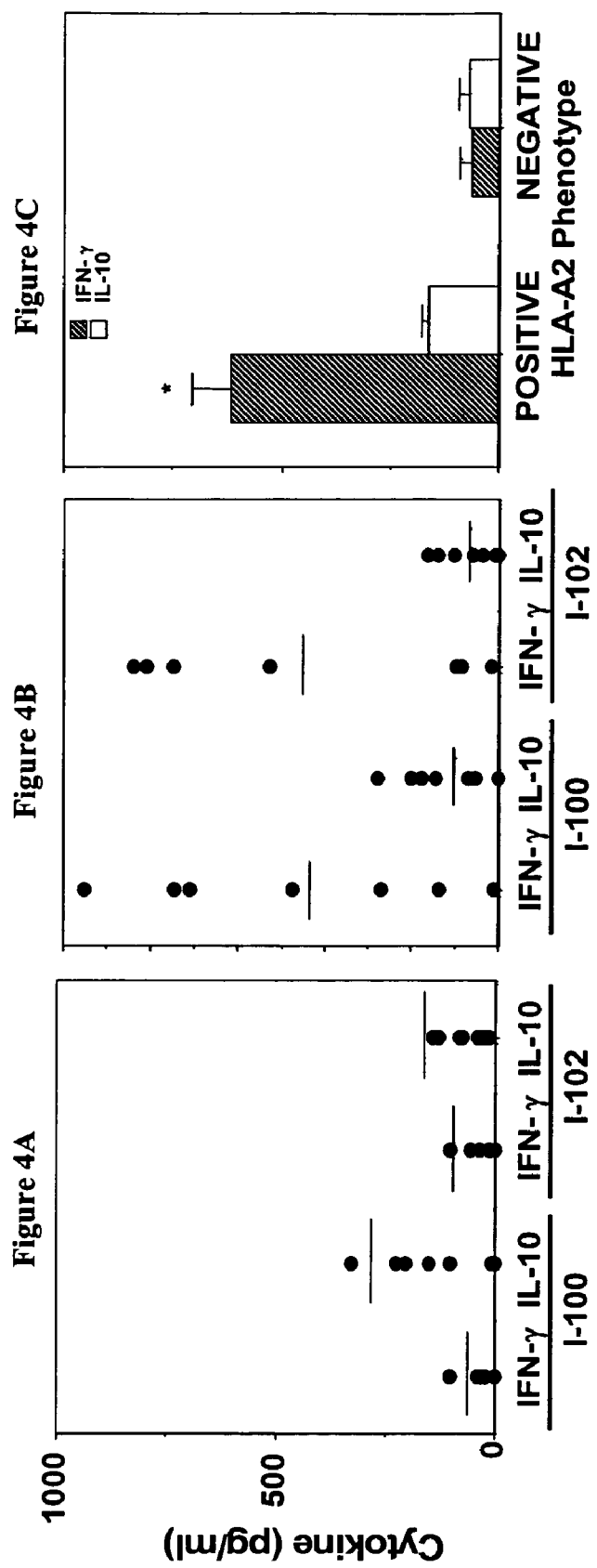

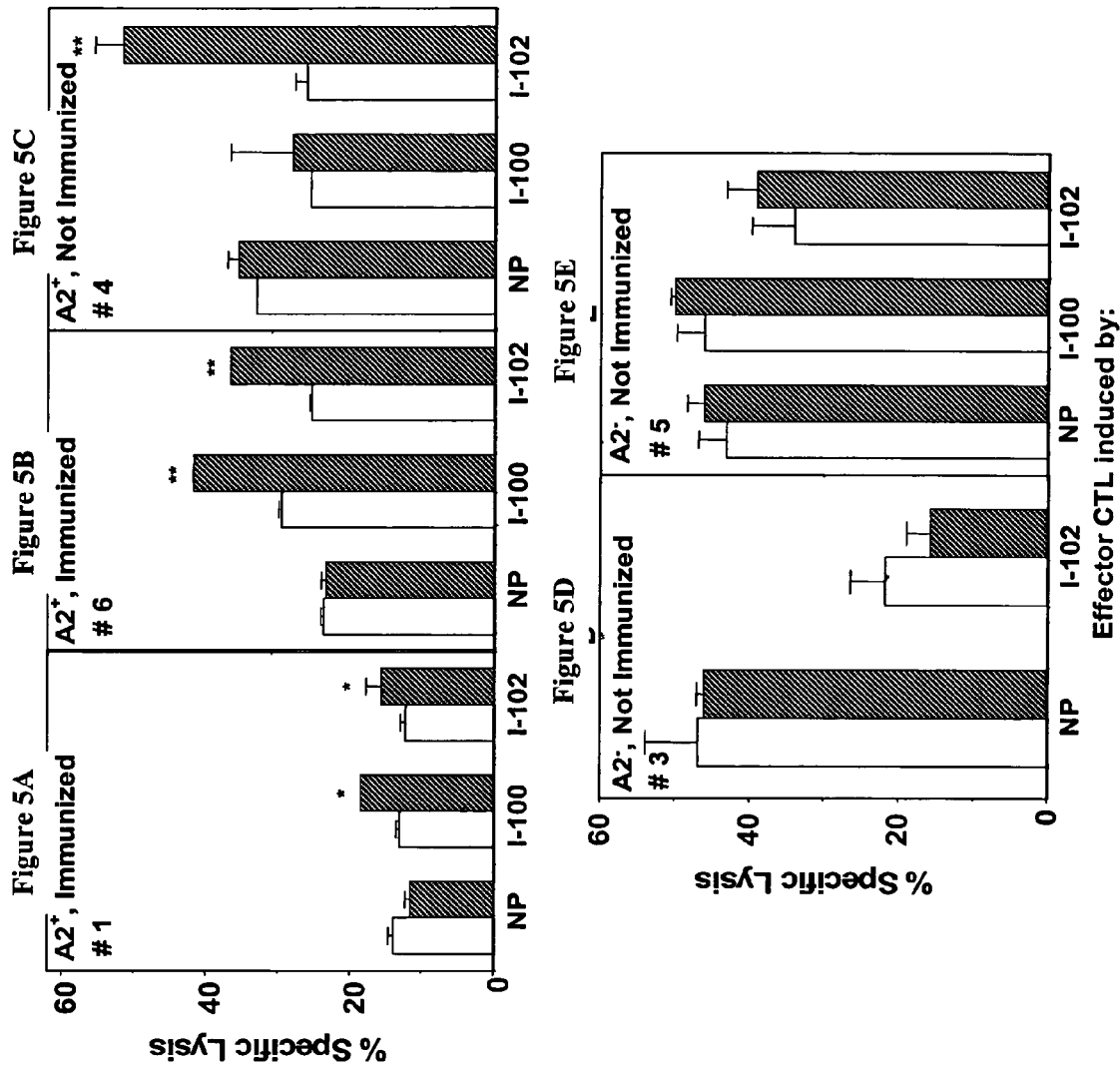

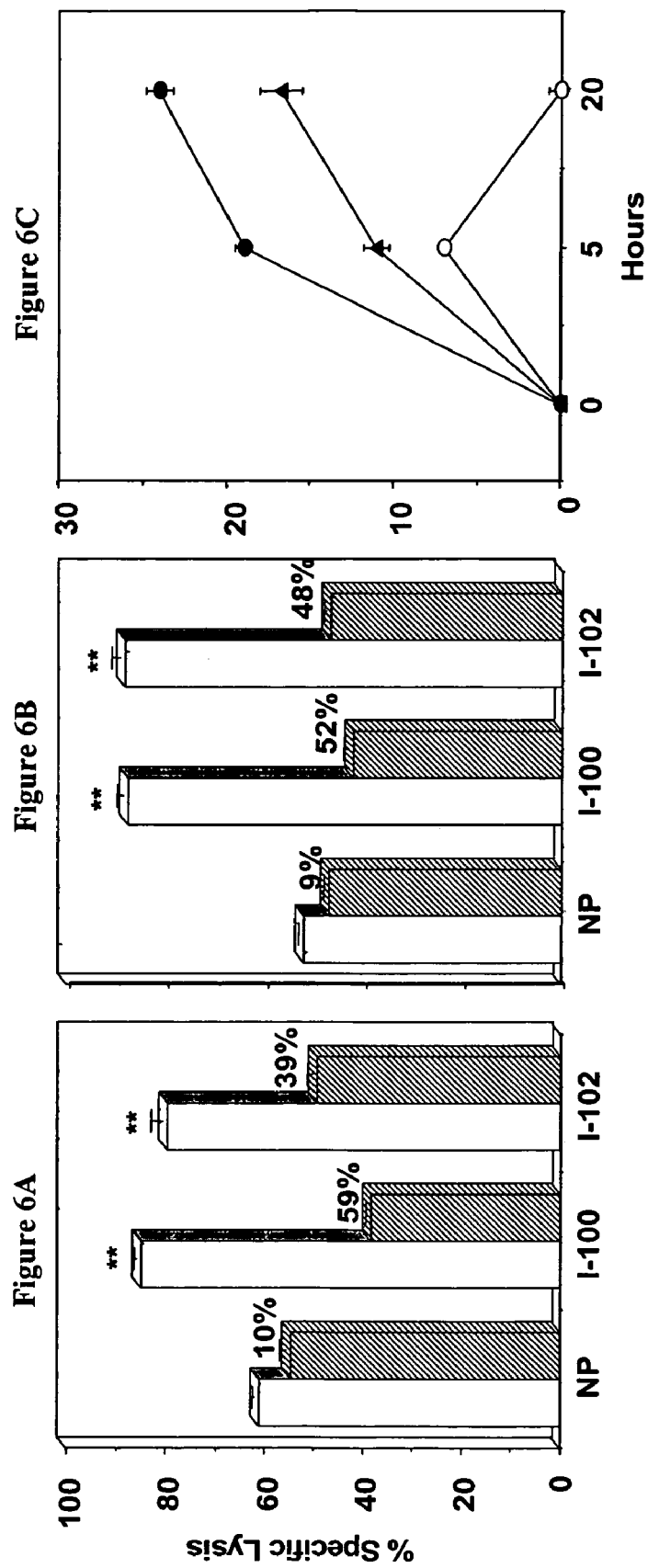

```
                              SEQUENCE LISTING

<160> NUMBER OF SEQ ID NOS: 26

<210> SEQ ID NO 1
<211> LENGTH: 20
<212> TYPE: PRT
<213> ORGANISM: mouse
<220> FEATURE:
<223> OTHER INFORMATION: mAb MF11-30

<400> SEQUENCE: 1

Lys Met Leu Leu Val Leu Leu Tyr Ser Lys Leu Ser Ser Gln Cys
                5                   10                  15

Ala Glu Asp Gln Thr
                20

<210> SEQ ID NO 2
<211> LENGTH: 21
<212> TYPE: PRT
<213> ORGANISM: mouse
<220> FEATURE:
<223> OTHER INFORMATION: mAb 105AD7

<400> SEQUENCE: 2

Asp Thr Leu Cys Tyr Thr Leu Leu Leu Thr Ile Pro Ser Arg Val
                5                   10                  15

Leu Ser Gln Val Thr Leu
                20  21

<210> SEQ ID NO 3
<211> LENGTH: 9
<212> TYPE: PRT
<213> ORGANISM: mouse
<220> FEATURE:
<223> OTHER INFORMATION: mAb MF11-30

<400> SEQUENCE: 3

Leu Leu Val Leu Leu Tyr Ser Lys Leu
                5               9

<210> SEQ ID NO 4
<211> LENGTH: 9
<212> TYPE: PRT
<213> ORGANISM: human
<220> FEATURE:
<223> OTHER INFORMATION: HMW-MAA
```

```
<400> SEQUENCE: 4

Leu Leu Gln Leu Tyr Ser Gly Arg Leu
                5                   9

<210> SEQ ID NO 5
<211> LENGTH: 9
<212> TYPE: PRT
<213> ORGANISM: mouse
<220> FEATURE:
<223> OTHER INFORMATION: mAb MF11-30

<400> SEQUENCE: 5

Ala Glu Asp Gln Thr Ala Val His Leu
                5                   9

<210> SEQ ID NO 6
<211> LENGTH: 9
<212> TYPE: PRT
<213> ORGANISM: human
<220> FEATURE:
<223> OTHER INFORMATION: HMA-MAA

<400> SEQUENCE: 6

Val Glu Asp Thr Phe Cys Phe His Val
                5                   9

<210> SEQ ID NO 7
<211> LENGTH: 9
<212> TYPE: PRT
<213> ORGANISM: mouse
<220> FEATURE:
<223> OTHER INFORMATION: mAb 105AD7

<400> SEQUENCE: 7

Thr Leu Cys Tyr Thr Leu Leu Leu Thr
                5                   9

<210> SEQ ID NO 8
<211> LENGTH: 9
<212> TYPE: PRT
<213> ORGANISM: human
<220> FEATURE:
<223> OTHER INFORMATION: CD55

<400> SEQUENCE: 8

Thr Leu Val Thr Met Gly Leu Leu Thr
                5                   9

<210> SEQ ID NO 9
<211> LENGTH: 10
<212> TYPE: PRT
<213> ORGANISM: mouse
<220> FEATURE:
<223> OTHER INFORMATION: 105AD7

<400> SEQUENCE: 9

Leu Leu Leu Thr Ile Pro Ser Arg Val Leu
                5                       10

<210> SEQ ID NO 10
<211> LENGTH: 10
<212> TYPE: PRT
<213> ORGANISM: human
<220> FEATURE:
<223> OTHER INFORMATION: CD55

<400> SEQUENCE: 10
```

```
Leu Leu Gly Glu Leu Phe Arg Leu Leu Leu
                 5                   10

<210> SEQ ID NO 11
<211> LENGTH: 8
<212> TYPE: PRT
<213> ORGANISM: mouse
<220> FEATURE:
<223> OTHER INFORMATION: 105AD7

<400> SEQUENCE: 11

Arg Val Leu Ser Gln Val Thr Leu
                 5            8

<210> SEQ ID NO 12
<211> LENGTH: 8
<212> TYPE: PRT
<213> ORGANISM: human
<220> FEATURE:
<223> OTHER INFORMATION: CD55

<400> SEQUENCE: 12

Arg Leu Leu Leu Leu Val Leu Leu
                 5            8

<210> SEQ ID NO 13
<211> LENGTH: 9
<212> TYPE: PRT
<213> ORGANISM: mouse
<220> FEATURE:
<223> OTHER INFORMATION: mAb MK2-23

<400> SEQUENCE: 13

Val Gln Phe Gly Gly Ser Arg Lys Leu
                 5                9

<210> SEQ ID NO 14
<211> LENGTH: 9
<212> TYPE: PRT
<213> ORGANISM: human
<220> FEATURE:
<223> OTHER INFORMATION: HMW-MAA

<400> SEQUENCE: 14

Val Ala Arg Gly Gly Arg Arg Leu Leu
                 5                9

<210> SEQ ID NO 15
<211> LENGTH: 10
<212> TYPE: PRT
<213> ORGANISM: mouse
<220> FEATURE:
<223> OTHER INFORMATION: mAb MK2-23

<400> SEQUENCE: 15

Val Arg Gln Ala Phe Glu Lys Lys Gly Leu
                 5                   10

<210> SEQ ID NO 16
<211> LENGTH: 10
<212> TYPE: PRT
<213> ORGANISM: human
<220> FEATURE:
<223> OTHER INFORMATION: HMW-mAA

<400> SEQUENCE: 16
```

Val Val Gln Ala Phe Arg Lys Gly Asn Leu
              5                   10

<210> SEQ ID NO 17
<211> LENGTH: 9
<212> TYPE: PRT
<213> ORGANISM: mouse
<220> FEATURE:
<223> OTHER INFORMATION: mAb 3H1

<400> SEQUENCE: 17

Glu Leu Val Lys Phe Gly Ala Ser Leu
              5               9

<210> SEQ ID NO 18
<211> LENGTH: 9
<212> TYPE: PRT
<213> ORGANISM: human
<220> FEATURE:
<223> OTHER INFORMATION: CE antigen

<400> SEQUENCE: 18

Glu Thr Ile Tyr Phe Asn Ala Ser Leu
              5               9

<210> SEQ ID NO 19
<211> LENGTH: 383
<212> TYPE: DNA
<213> ORGANISM: mouse
<220> FEATURE:
<223> OTHER INFORMATION: MF11-30 VH sequence

<400> SEQUENCE: 19
aagatgcttc tggttttgct gtactccaag ctttcttccc agtgcgctga agatcagact      60
gctgtgcacc tacagagcct gtccatcaca tgcactgtct ctggttcgca ttatccagat     120
ataatgtaca ctgggttcgc caagcctcca ggaaagggtc tggagtggct gggaatgata     180
tggggtgctg gaagtacaga ctataattca gctctcaaat ccagactgac catcaacaag     240
gacaactcca agagccaagt tttcttaaaa atgaacagtc tgcaaattga tgacacagca     300
tgtactactg tgccagagag agagagagac atggtaaccc gtttgctggc caagggactc     360
tggtcactgt ctctgcagcc aaa                                             383

<210> SEQ ID NO 20
<211> LENGTH: 130
<212> TYPE: PRT
<213> ORGANISM: mouse
<220> FEATURE:
<223> OTHER INFORMATION: MF11-30 VH sequence

<400> SEQUENCE: 20

Lys Met Leu Leu Val Leu Leu Tyr Ser Lys Leu Ser Ser Gln Cys
              5                   10                  15

Ala Glu Asp Gln Thr Ala Val His Leu Gln Ser Leu Ser Ile Thr
              20                  25                  30

Cys Thr Val Ser Gly Ser His Tyr Phe Asp Ile Met Tyr Thr Gly
              35                  40                  45

Phe Ala Lys Phe Phe Gly Lys Gly Leu Glu Trp Leu Gly Met Ile
              50                  55                  60

Trp Gly Ala Gly Ser Thr Asp Tyr Asn Ser Ala Leu Lys Ser Arg
              65                  70                  75

Leu Thr Ile Asn Lys Asp Asn Ser Lys Ser Gln Val Phe Leu Lys

```
                    80               85                90
Met Asn Ser Leu Gln Ile Asp Asp Thr Ala Met Tyr Tyr Cys Ala
                95                  100                 105

Arg Glu Arg Glu Arg His Gly Asn Phe Phe Ala Tyr Trp Gly Gln
                110                 115                 120

Gly Thr Leu Val Thr Val Ser Ala Ala Lys
                125                 130

<210> SEQ ID NO 21
<211> LENGTH: 305
<212> TYPE: DNA
<213> ORGANISM: mouse
<220> FEATURE:
<223> OTHER INFORMATION: MF11-30 VL sequence

<400> SEQUENCE: 21
aaaccatgcc ctgtagctag tatgtcgatc accttgctgc tagcagcaca ctctgagcag    60
ctaagttata tatgtaagct gtaccacaga acagacagca ccaactccta tctagctgcg   120
tccaatctag aatctggatc ccagccaggt ttagtggcag tgggtctggg acagacttca   180
ccctcaacat ccatcctgtg gaggaggagg atgctgcaac ctattactgt cagcaaagta   240
atgaggatcc gtacacgttc ggaggggggga ccaagctgga aataaaacgg gctgatgctg   300
cacca                                                                305

<210> SEQ ID NO 22
<211> LENGTH: 103
<212> TYPE: PRT
<213> ORGANISM: mouse
<220> FEATURE:
<223> OTHER INFORMATION: MF11-30 VL sequence

<400> SEQUENCE: 22

Lys Phe Cys Phe Val Ala Ser Met Ser Ile Thr Leu Leu Leu Ala
                5                   10                  15

Ala His Ser Glu Gln Leu Ser Tyr Ile Cys Lys Leu Tyr His Arg
                20                  25                  30

Thr Asp Ser Thr Asn Ser Tyr Leu Cys Cys Val Gln Ser Arg Ile
                35                  40                  45

Trp Ile Phe Ala Arg Phe Ser Gly Ser Gly Ser Gly Thr Asp Phe
                50                  55                  60

Thr Leu Asn Ile His Phe Val Glu Glu Glu Asp Ala Ala Thr Tyr
                65                  70                  75

Tyr Cys Gln Gln Ser Asn Glu Asp Phe Tyr Thr Phe Gly Gly Gly
                80                  85                  90

Thr Lys Leu Glu Ile Lys Arg Ala Asp Ala Ala Phe Thr
                95                  100         103

<210> SEQ ID NO 23
<211> LENGTH: 9
<212> TYPE: PRT
<213> ORGANISM: mouse
<220> FEATURE:
<223> OTHER INFORMATION: mAb MF11-30

<400> SEQUENCE: 23

Leu Leu Val Leu Leu Tyr Ser Lys Leu
                5               9

<210> SEQ ID NO 24
```

```
<211> LENGTH: 9
<212> TYPE: PRT
<213> ORGANISM: human
<220> FEATURE:
<223> OTHER INFORMATION: HMW-MAA

<400> SEQUENCE: 24

Leu Leu Gln Leu Tyr Ser Gly Arg Leu
                5                 9

<210> SEQ ID NO 25
<211> LENGTH: 10
<212> TYPE: PRT
<213> ORGANISM: artificial sequence
<220> FEATURE:
<221> NAME/KEY:
<222> LOCATION:
<223> OTHER INFORMATION: designed peptide
<220> FEATURE:
<223> OTHER INFORMATION: MF11-30 variant sequence

<400> SEQUENCE: 25

Leu Leu Gln Leu Gly Tyr Ser Gly Arg Leu
                5                  10

<210> SEQ ID NO 26
<211> LENGTH: 9
<212> TYPE: PRT
<213> ORGANISM: mouse
<220> FEATURE:
<223> OTHER INFORMATION: VH sequence

<400> SEQUENCE: 26

Ala Ala Gly Ile Gly Ile Leu Thr Val
                5                 9
```

METHOD FOR IDENTIFYING AND DESIGNING IMMUNOGENIC PEPTIDES

This application claims priority to U.S. provisional application Ser. No. 60/630,718, filed Nov. 24, 2004, the disclosure of which is incorporated herein by reference.

FIELD OF THE INVENTION

The present invention is generally directed to cancer therapy and more particularly to identification and/or design of peptides which are more immunogenic than tumor antigens.

BACKGROUND OF THE INVENTION

The use of idiotype specific antibodies, ie, anti-idiotypic antibodies, as immunogens is based on the rationale put forward by the idiotype-network theory (Jerne, N K, Eur J Immunol 34:1243-50, 2004; Jeme, N K, et al., EMBO J 1:243-7, 1982). According to this theory, an antigen (Ag) induces an Ab (Ab1) specifically recognizing a defined amino acid sequence and/or structural motif unique to the Ag.

Because the Ag-binding sequence of Ab1 is unique, Ab1 is seen as foreign by the immune system which has produced it. As a consequence, the immunized host generates another Ab (Ab2), which recognizes specifically the Ag-binding sequence of Ab 1. Since only certain areas (the idiotopes) of Ag-binding regions of antibodies differ between Ab1 and antibodies of other specificities present in the host, it is believed that Ab2 recognizes only the Ag-binding sequence on Ab1. Therefore, the Ag binding sequence of Ab1 recognizes several amino acids of the Ag, and it is therefore generally believed that Ab2 carries the "internal image" of the Ag. (Jerne, N K, Eur J Immunol 34:1243-50, 2004; Jerne, N K, et al., EMBO J 1:243-7, 1982). Based on this rationale, a number of immunotherapy studies have used Ab2 as an anticancer agent (Pride, M W, et al., Clin Cancer Res 4:2363-70, 1998). However, the role of idiotype-specific immune responses in regulation of tumor proliferation and metastasis is poorly understood.

One hypothesis is that Ab2 stimulates the immune system to generate new antibodies to the "internal image" of the Ag. These Ab, generally termed Ab3, once induced, will interact with the inducing Ag on the tumor cell with higher affinity than Ab 1. However, the question is more complex than it initially appears. For example, if the tumor Ag and the Ab2 share linear sequence homology, then the resulting T cells, as self-reactive T cells, should be tolerized or deleted.

While the basis of structural mimicry between an Ag and the corresponding anti-id antibody is unclear, one possibility is represented by the structural basis of the interactions of a tumor associated antigen (TAA) and corresponding anti-id antibody with the same area of the antigen combining site of the anti-TAA antibody. These interactions are likely to involve side chains of amino acids which can form strong H-bonds (involving OH groups) and even stronger electrostatic interactions between positively/negatively charged terminal groups of the side chains and reversely charged groups in Ag-binding regions of Ab and of TCR. However, peptides derived from TAA are all generally weak inducers of CTL response (Waters, S. J., et al., Cell Immunol., 111:87-93, 1988).

Thus, to pursue novel immunotherapeutic approaches to the treatment of cancer, there is an ongoing need for determining peptide sequences that can elicit a CTL response against a particular antigen, where the peptides stimulate a CTL response that is greater than the CTL response stimulated by a peptide derived from the antigen.

SUMMARY OF THE INVENTION

The present invention provides a method for identifying peptides for use in immunotherapeutic approaches. The peptides are identified as short regions (8-20 amino acid) of an anti-idiotypic antibody having homology with a region of the corresponding antigen and further comprising one or more HLA binding motif(s). These peptides have the ability to stimulate a cytotoxic T lymphocyte (CTL) response. The peptide regions of the ant-id antibodies may be modified to further enhance the immunogenic response.

In one embodiment, the method comprises obtaining the amino acid sequences of the VH and/or VL portions of the anti-idiotypic antibody (Ab2), obtaining the sequence of the antigen, comparing the sequences to identify candidate homologous regions within the Ab2 (i.e., regions that show homology to regions of the corresponding antigen), and further identifying those candidate homologous regions of Ab2 which also comprise HLA binding motifs. These peptides are then tested for their ability to stimulate a CTL response. Preferred peptides are those which stimulate a greater CTL response than the corresponding antigen or a peptide derived from the antigen.

In another embodiment, the present invention also provides peptides identified by the method. In this regard, the peptide sequences are homologous to a portion of Ab2 and a portion of the antigen, and further comprise an HLA binding motif.

In another embodiment, the method further comprises modifying the peptide sequences identified as homologous regions of Ab2 to further enhance their ability to stimulate a CTL response.

This invention also provides a method for using the peptides identified by the method in generating an increased immunogenic response in an individual against the tumor antigen. The method comprises administering to the individual an amount of peptide which has homology to a portion of the antigen and to a portion of an Ab2 which mimics an epitope on the antigen, and wherein the peptide comprises an HLA binding motif, effective to stimulate a CTL mediated immune response against the antigen.

BRIEF DESCRIPTION OF THE DRAWINGS

FIG. 2 provides the anti-id mAb MF11-30 $V_H$ and $V_L$ nucleotide and deduced amino acid sequences. The numbering of residues and positioning of CDRs (complementarity determining regions) are based on the Kabat Numbering Scheme and the Kabat definition of CDRs at website: www.bioinf.org.uk/abs/. Italicized letter codes of amino acids represent CDR. Underlined letter codes of amino acid indicate positions at which insertions occur, and are further indicated by parenthetical annotations in the nucleotide sequence.

FIGS. 3A-3D are graphical representations of levels of IFN-γ and IL-10 secreted by PBMC obtained from HLA-A2$^+$ patient # 6 following in vitro stimulation with peptides I-100 and I-102 (FIGS. 6A and 6B, respectively). IFN-γ (▲) and IL-10(■) levels (pg/ml) in media harvested from cultures 72 h after 1° STIM with increasing concentrations of peptides I-100 (FIG. 3A) and I-102 (FIG. 3B). IFN-γ (FIG. 3C) and IL-10 (FIG. 3D) levels (pg/ml) in media harvested from cultures following 2° STIM with peptides I-100, I-102 and F119 (25 μg/ml).

FIGS. 4A-4C are graphical representations of levels of IFN-γ and IL-10 secreted by PBMC from HLA-A2$^+$ and HLA-A2$^-$ patients following 1° (FIG. 4A) and 2° (FIG. 4B)

Figure 1:
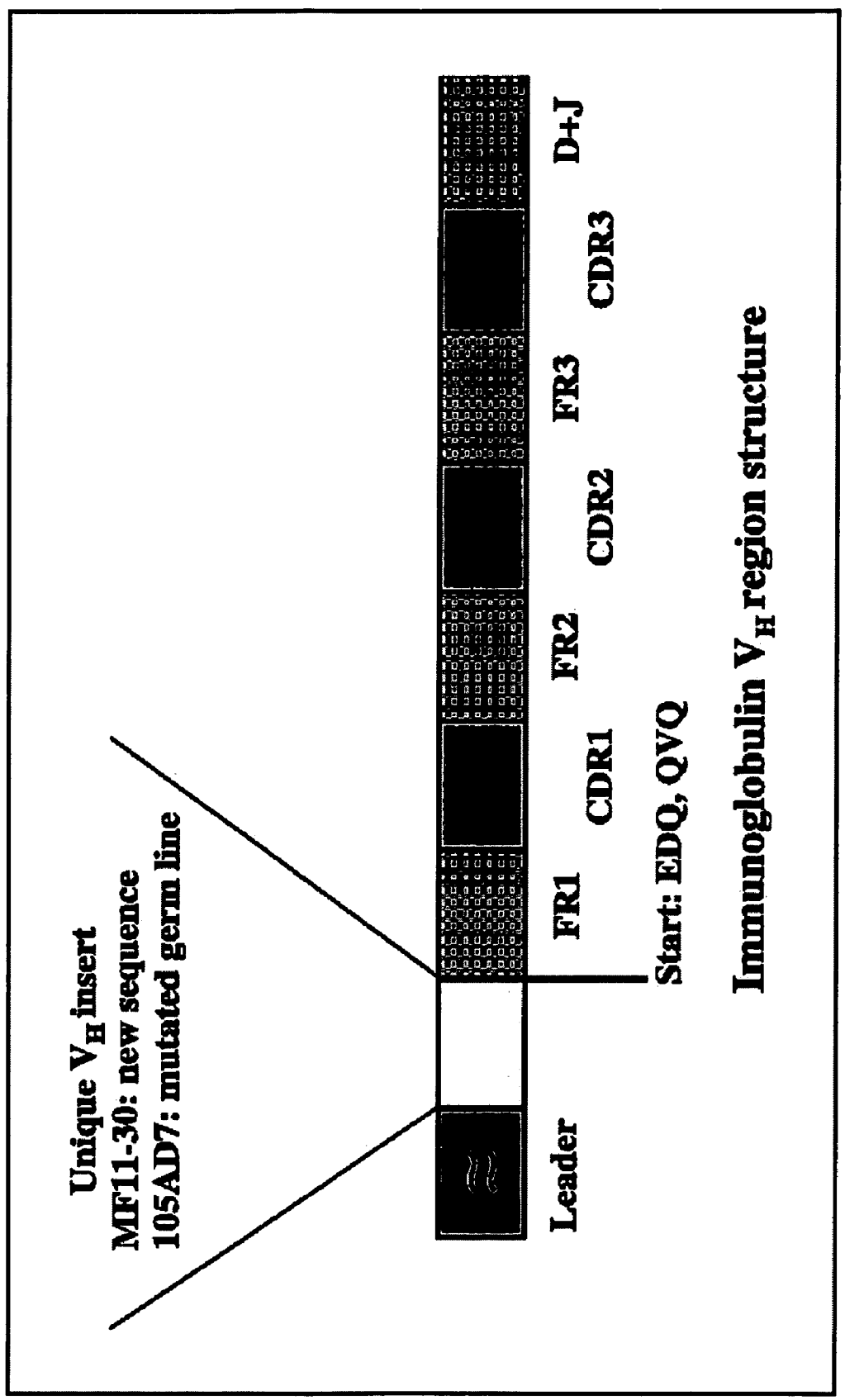
FIG. 1 is a graphical depiction of the $V_H$ region structure. The relative positions of unique regions for Ab2 MF11-30 and Ab2 105Ad7 are indicated.

STIM with peptides I-100 and I-102 (25 μg/ml) (FIG. 4C). IFNγ levels (pg/ml) secreted by PBMC from HLA-A2⁺ patients were significantly (*p<0.007) higher than those from HLA-A2⁻ patients. IL-10 levels were not different between these two groups of patients.

FIGS. 5A-5E are graphical representations of cytolytic activity of NP, I-100 and I-102-CTL from HLA-A2 immunized patients # 1 and # 6 (FIGS. 5A and 5B, respectively) and from HLA-A2, non-immunized patient # 4 (FIG. 5C) against T2-NP (■) and T2-I-100 (□) targets. FIG. 5D depicts lytic activity of NP- and I-102-CTL from HLA-A2⁻ patient #3 against T2-NP (■) and T2-I-100 (□) targets. FIG. 5E depicts CTL lysis by NP-, I-100-, and I-102-CTL effectors from HLA-A2⁺ patient #5 against T2-I-100 targets. The E:T ratio was 30:1 in a 4 hour 51Cr release assay; bars, ±SD.

FIGS. 6A-6C are graphical representations of the similarity of the epitope recognized by I-100- and I-102-CTL as demonstrated by lysis of A375SM melanoma cells. FIG. 6A shows significant (p<0.001) inhibition by T2-I-100 cells (■) of lysis of A375SM cells by I-100- and I-102-CTL from HLA-A2⁺ patient #1. NP-, I-100, and I-102 on the abscissa indicate corresponding CTL effectors. NP-CTL indicates CTL stimulated by T2 cells and IL-2 without addition of peptides. FIG. 6B shows significant (**p<0.001 vs NP-ST effectors) inhibition by anti-HLA-A2 mAb MA2.1 of lysis of A375SM melanoma cells by I-100- and I-102-CTL from HLA-A2⁺ patient #6 A375SM. The E:T ratio was 20:1 in a 20 h $^{51}$Cr release assay. FIG. 6C depicts the kinetics of A375SM melanoma cell lysis by NP-CTL (○), I-100-CTL (●), and I-102-CTL (▲). CTL were incubated with target cells for up to 20 h.

DETAILED DESCRIPTION OF THE INVENTION

The present invention is directed to identification of short regions nested within the sequence of anti-idiotypic antibodies that share homogy with an epitope of the corresponding antigen, contain HLA binding motifs and are capable of stimulating a CTL response. Peptides corresponding to such identified short regions of the anti-id antibodies may be modified further to enhance the ability to stimulate an immunogenic response.

Anti-idiotypic monoclonal antibodies are also referred to herein as "Ab2" and "anti-Id antibodies.

The terms "antigen corresponding to an anti-idiotypic antibody" or the "corresponding antigen" are used herein to refer to the antigen which is mimicked by the Ab2. It is considered that Ab2s carriy the 'internal image' of an epitope of the antigen.

"Homologous regions" or "homology" as referred to herein is intended to indicate that the amino acid sequences are at least 55% identical or are similar in charge, OH group and side chain.

The method of the present invention generally comprises:
1) obtaining the amino acid sequences of VH and/or VL portions of an Ab2;
3) obtaining the amino acid sequence of the antigen;
4) comparing the sequences of the Ab2 and the antigen to identify regions of homology between Ab2 and the antigen; and
5) within the identified homologous regions of the anti-id antibody, further identifying HLA binding motifs, such that the identified sequences which are homologous to Ab2 and the antigen, and which comprise HLA binding motifs, define peptides that are capable of stimulating a CTL response to the antigen. It is preferred that the CTL response stimulated by the anti-id antibody peptides is greater than the CTL response elicited by the antigen.

It will be appreciated by those skilled in the art that the particular order of steps described above is not critical. For example, the same result could be achieved by first identifying HLA binding motifs within short regions of the anti-id antibody or the corresponding antigen and then determining if the short regions containing the HLA binding motifs also share homology with the antigen or the anti-id antibody respectively.

The NH$_2$-terminal regions of the heavy (H) and light (L) chains of an antibody are of particular relevance to this invention as these regions have been implicated in antigen recognition. Because these regions recognize diverse amino acid sequences, and maintain their folding, the first 120 to 140 NH$_2$-terminal amino acids define the variable region of the heavy (V$_H$) and light (V$_L$) chains. Therefore, short regions nested within the sequence of the Ab2 which show homology to a region of the antigen may be identified in the V$_H$ or the V$_L$ region.

Further, the Vh and the VL contains three complementarity-determining regions designated as complementarity determining regions, CDR1, CDR2, and CDR3. These three regions are more mutated compared with the intervening regions, which are designated as framework regions (FRs). The short regions on the Ab2 showing homology to the antigen and containing HLA binding motifs may be present or may straddle the CDRs or the FRs.

Differences in the antigen structure translate in amino acid differences in these regions. When an antibody recognizes a protein in its native form, framework regions are likely to be involved in antigen binding (Li Y, et al., J Mol Biol 256:577-589, 1996; Potter K N, et al., Mol Immunol 35:1179-1187, 1998). Considering that an antibody against a protein has high affinity for its ligand, the specific recognition is due to involvement of both framework region and CDR3. Thus, the idiotopes/internal images of the antigen may be present in framework region and in CDR3 of Ab2. Therefore, areas within or near the FR1 or the CD3 region or in the junction region which are before the FR1 region between the leader and the FR1 region are particularly useful for evaluating HLA binding motifs and antigen homology.

In a variation of the above embodiment, the sequence of the Vh and the VL regions of an Ab2 are searched for the presence of unique sequences—i.e., sequences that show no homology or show minimal homology to sequences within other IgGs. These unique Ab2 sequences are then evaluated for homology to the antigen sequence and for the presence of HLA binding motifs. For example, in one embodiment, the Ab2 sequence is analyzed for unique VH peptide sequences preceding the FR1 region (FIG. 1).

The peptides corresponding to the identified short regions of Ab2 are between 8-20 amino acids long. This is generally considered a suitable length for generating an immunogenic response. In individual embodiments, the peptides may be of any length between 8 and 20. In a particular embodiment, the peptides are between 9 to 11 amino acids long.

HLA binding motifs for which the Ab2 and antigen can be analyzed include HLA-A, HLA-B, HLA-C, HLA-DPA1, HLA-DPB1, HLA-DQA1, HLA-DQB1, HLA-DRA, and HLA-DRB1, and including their respective subclasses. Critical residues that correspond to motifs required for specific binding to HLA antigen molecules have been identified. (see also, Sette, A., et al. Curr. Opin. Immunol. 4:79, 1992; Sinigaglia, F. and Hammer, J., Curr. Biol. 6:52, 1994; Engelhard, V. H., Curr. Opin. Immunol. 6:13, 1994). The HLA-A includes the subclasses the HLA-A1, HLA-A2 and HLA-A3 motifs. The HLA-A1 motif is characterized by the presence of T, S, or M as a primary anchor residue at position 2 and the presence of Y as a primary anchor residue at the C-terminal position. Alternatively, a primary anchor residue may be present at position 3 rather than position 2. The HLA-A2 binding motif is characterized by hydrophobic aliphatic residues at positions 1, 2 and 9 and an aromatic residue at position 6. The HLA-A3 binding motif is characterized by the presence of L, M, V, I, S, A, T, F, C, G, or D as a primary anchor residue at position 2 and the presence of K, Y, R, H, F, or A as the primary anchor residue at the C-terminal position.

The present invention also provides the design of modified peptide sequences based upon the peptide sequences identified from the comparison of the Ab2, the antigen sequences and the HLA motifs. Generally, the 3-5 COOH terminus residues should be kept the same as the antigen epitope so as to maintain recognition of the same TCR. Introduction of charged residues or shifting the position of amino acid residues in the peptide by amino acid insertions or deletions can then be used to generate peptides be effective stimulating a T-cell response. Such modifications are based upon the HLA binding motif identified in the Ab2 and the antigen such that the affinity of the peptide for the particular HLA is improved, particularly through an increase in H bonding between the peptide and the HLA molecule. Additionally, peptides can also be made resistant to proteasome destruction.

Methods for obtaining Ab2 are well known to those skilled in the art. For example, the hybridoma technique originally described by Kohler and Milstein (1975, Nature 256:495-497) and the human B-cell hybridoma technique (Kozbor et al., 1983, Immunology Today 4:72) are suitable methods for obtaing Ab2. Further, Kusama et al (J. Immunol., 1989 Dec. 1;143(11):3844-52) have described the generation of Ab2 for HMW-MAA. Ab2 can be purified by well known techniques, such as by ammonium sulfate precipitation from hybridoma supernatant followed by column chromatography. Alternatively, the method can be practiced using known sequences of Ab2 obtained from databases or the relevant literature.

Methods for determining the sequence of an idiotype binding region of Ab2 are known. For example, a suitable protocol for determining the amino acid sequence of an Ab2 VH or VL region is disclosed in Iwasaki, et al. Eur. J. Immunol., 24:2874-2881, 1994. The amino acid sequence of the antigen may be determined by standard amino acid analysis techniques or by chemical sequencing (e.g., the Edman degradation procedure). Further, the amino acid sequence of Ab2 VH and/or VL regions can be determined by sequencing the genomic DNA or cDNA encoding the Ab2 according to established techniques. In one embodiment, only the VH amino acid sequence need be obtained.

Methods for comparing amino acid sequences, such as the sequence of a peptide antigen and an idiotope binding region of Ab2 are also known. Such methods include the use of amino acid sequence comparison software programs, such as BLOSUM62 (available at www.us.expasy.org/tools), proteomics programs available from Accelrys, Inc. and sequence analysis programs available from the BioInformatics & Molecular Analysis Section of the National Institutes of Health.

In one embodiment, the Ab2 sequence is analyzed for unique VH peptide sequences preceding the FR1 region by comparing the VH region preceding the FR1 region with a database of immunoglobulin sequences. A unique sequence should be non-existent in the database immunoglobulin sequences with regard to corresponding VH regions.

Methods for identifying HLA binding motifs in the Ab2 and antigen amino acid sequences are also known. In this regard, the present invention contemplates searching for binding motifs for any desired HLA in the Ab2 and in the antigen.

For analyzing sequences for the presence of HLA binding motifs, amino acid sequences of Ab2 and the antigen can be analyzed for homology with particular HLA binding motifs using publicly available databases and computer programs, such the HLA Ligand/Motif Database, accessible at hlaligand.ouhsc.edu/LigandDB/servlet/GenerateForm Servlet?form_type=index, or the Biores database, available at bioresearch.ac.uk/browse/mesh/D006680.html. (See also e.g., Sette, A. and Grey, H. M., Curr. Opin. Immunol. 4:79, 1992; Sinigaglia, F. and Hammer, J., Curr. Biol. 6:52, 1994; Engelhard, V. H., Curr. Opin. Immunol. 6:13, 1994Kast, W. M. et al., J. Immunol., 152:3904, 1994).

The peptides of the invention can be prepared by any technique known to those skilled in the art or those later developed, such as by recombinant genetic techniques or by chemical synthesis. For example, peptides can be prepared using the solid-phase synthetic technique (Merrifield, J. Am. Chem. Soc., 15:2149-2154 (1963); M. Bodanszky et al., (1976) Peptide Synthesis, John Wiley & Sons, 2d Ed.; Kent and Clark-Lewis in Synthetic Peptides in Biology and Medicine, p. 295-358, eds. Alitalo, K., et al. Science Publishers, (Amsterdam, 1985). A summary of peptide synthesis techniques may be found in J. Stuart and J. D. Young, Solid Phase Peptide Synthesis, Pierce Chemical Company, Rockford, Ill. (1984). The synthesis of peptides by solution methods may also be used, as described in The Proteins, Vol. II, 3d Ed., p. 105-237, Neurath, H., et al., Eds., Academic Press, New York, N.Y. (1976). In general, the synthesis of the peptides involves the sequential addition of one or more amino acid residues or suitable protected amino acid residues to a growing peptide chain. Typically, the carboxyl group of the first amino acid residue is pre-attached to a solid support, the amino group being protected by a first, selectively-removable protecting group. A second, different, selectively removable protecting group is utilized with amino acids containing a reactive side group, such as lysine. After the removal of the first protecting group, the carboxyl group of the second amino acid is coupled to the amino group of the first amino acid. The process is then repeated until the peptide is complete, at which time the peptide is removed from the solid support and purified. The synthesized peptides may be substantially purified by preparative high performance liquid chromatography (e.g., Creighton, T. (1983) Proteins, Structures and Molecular Principles, W H Freeman and Co., New York, N.Y.) or other comparable techniques available in the art. The composition of the synthetic peptides may be confirmed by amino acid analysis or sequencing.

Once candidate peptide sequences have been identified and the peptides are synthesized, it is preferable to assess their affinity for a particular HLA. Accordingly, a variety of assays to detect and quantify the affinity of interaction between peptide and HLA are known to those skilled in the art. (Sette, A. and Grey, H. M., Curr. Opin. Immunol. 4:79, 1992; Sinigaglia, F. and Hammer, J., Curr. Biol. 6:52, 1994; Engelhard, V. H., Curr. Opin. Immunol. 6:13, 1994). Further, the affinity of the peptides for particular HLAs can be assessed using computer programs.

It is also preferable to test the identified peptide sequences for the ability to elicit a T-cell response. Such testing can be performed according to established techniques. Representative assays for this purpose include proliferation assays, lymphokine secretion assays, direct cytotoxicity assays, and limiting dilution assays. For example, antigen-presenting cells that have been incubated with a peptide can be assayed for the ability to induce CTL responses in responder cell populations. The antigen-presenting cells can be normal cells such as peripheral blood mononuclear cells or dendritic cells.

Peripheral blood lymphocytes may be used as the responder cell source of CTL precursors. The appropriate antigen-presenting cells are incubated with peptide and the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

In one embodiment of this invention, individuals having tumors such as primary tumors, mestatic disease or both, or individuals who are in remission may be administered peptides identified by the present invention. This method comprises administering to an individual an amount of peptide effective to inhibit the formation of tumors and/or kill cancer cells. The peptides may be formulated with a suitable adjuvant in order to enhance the immunological response. Further, the peptides can be administered in a conventional dosage form prepared by combining the peptides with a standard pharmaceutically acceptable carrier or diluent according to known techniques. It will be recognized by one of skill in the art that the form and character of the pharmaceutically acceptable carrier or diluent is dictated by the amount of peptide with which it is to be combined, the route of administration and other well-known variables, such as the size of the individual and the stage of the disease. Further, various methods known to those skilled in the art may be used to introduce the peptide formulations to an individual. These methods include intradermal, intramuscular, intraperitoneal, intravenous, subcutaneous, and intranasal routes.

While not intending to be bound by any particular theory, it is considered that administration of the peptides, identified according to the present invention, to individuals diagnosed with a tumor will stimulate the activation and differentiation of CTLs that recognize related epitopes including the tumor antigen. Therefore, it is expected that the functional avidity of the CTLs for the tumor antigens will be increased.

The following Examples are meant for purposes of illustration and are not meant to limit the scope of the invention in any way.

EXAMPLE 1

This Example discloses the VH and VL sequences of anti-id mAb MF11-30 and demonstrates the identification of peptide sequences comprising homologous HMW-MAA and anti-id mAb MF11-30 sequences, which homologous sequences also comprise HLA-A2 binding peptide motifs.

The VH and VL nucleotide and deduced amino acid sequences of anti-id mAb MF11-30 are shown in FIG. 2. The anti-HLA-A2.1 mAbs MA2.1 and BB7.2 (McMichael, et al. Hum Immunol 1980;1:121-9; Hoga, n et al. J Immunol 1989; 142:2097-104) were purified from the corresponding hybridoma supernatants by ammonium sulfate precipitation followed by column chromatography. Both anti-HLA-A2 mAb secreting hybridomas were obtained from American Type Culture Collection (Rockville, Md.). FITC-conjugated isotype-specific antimouse IgG and all of the other antibodies used herein were purchased from BD PharMingen (La Jolla, Calif.) The VH and VL sequences were determined using standard techniques as described previously (Iwasaki, et al. Eur J Immunol 1994;24:2874-81.).

For FIG. 2, the numbering of residues and positioning of CDRs (complementarity determining regions) in anti-id mAb MF11-30 VH and VL sequences are based on the Kabat Numbering Scheme and the Kabat definition of CDRs at website: www.bioinf.org.uk/abs/. Italicized letter codes of amino acids represent CDR. Underlined letter codes of amino acid indicate positions at which insertions occur. The VH nucleotide sequence is provided as SEQ ID NO:19. The VH amino acid sequence is provided as SEQ ID NO:20. The VL nucleotide sequence is provided as SEQ ID NO:21. The VL amino acid sequence is provided as SEQ ID NO:22.

The VH gene segment of the mAb MF11-30 shows high homology with the Q52 VH gene family. The D gene segment is part of the DSP2 mini-gene family. The JH gene segment is derived from the JH3 family. The VL gene segment shows homology with subgroup III of the VK gene family. The JK gene segment is 100% homologous with the JK2 mini-gene.

The amino acid sequences of the mAb MF11-30 VH and VL were compared with the published amino acid sequence of the HMW-MAA core protein (Pluschke et al., Proc Natl Acad Sci USA 1996;93: 710-5) using the program BLOSUM62 from the ExPASy website (Livingston et al. Cancer Immunol Immunother 1997, 45:10-9). Partial (between 20% and 40%) homology between these two proteins was observed only on short stretches of 10-17 amino acids. However, HLA-A2 binding motifs were not identified in these areas of homology.

We then searched the amino acid sequence of mAb MF11-30 VH and VL for HLA-A2 binding motifs, using the program by Taylor et al. available at http://bimas.dcrt.nih-.gov. The sequence VH (3-11) LLVLLYSKL (SEQ ID NO:23) in the framework region 1 met the criteria of an HLA-A2 binding peptide, i.e., hydrophobic aliphatic residues at positions 2 and 9, as well as hydrophobic aliphatic residue at position 1 and aromatic residue at position 6. This peptide had the highest binding affinity for HLA-A2 Ag of all VH peptides. Table 1 shows an alignment of anti-id mAb and HMW-MAA amino acid sequences in homologous areas; "b" indicates gaps introduced to illustrate alignment; "Score" indicates the calculated binding affinity to HLA-A2 Ag; "Code" represents the name of the peptide sequence. Table 3 in the left column provides alternative names for the peptides used herein, in addition to the terms under "Code."

TABLE 1

| (Est.t½) | 1 2 3 4 5 6 7 8 9 10 | Code | Score |
|---|---|---|---|
| MF11-30, VH(3-11) (SEQ ID NO: 23) | L L V L L Y S-$^b$ K L | I-100 | 54.75 |
| HMW-MAA, 76-84, wt (SEQ ID NO: 24) | L L Q L- Y S G R L | I-101 | 4.75 |
| HMW-MAA 76-84, variant (SEQ ID NO: 25) | L L Q L G Y S G R L | I-102 | 4.75 |

Analysis of the VH amino acid sequence with proteasome digestion programs (Toes, et al. J. Exp Med 2001; 194:1-12; Nielsen, et al. Protein Sci 2003;5:1007-17) indicated that this peptide is protected from proteasome digestion (data not shown). A search in the databases using the FASTA.3 program identified only few partially homologous sequences with the VH (3-11) in immunoglobulins and other proteins (data not shown) indicating that this peptide sequence was "idiotypic" for mAb MF11-30.

The VH3 (3-11) sequence was used for homology search in HMW-MAA. We found a partially homologous peptide (five of nine residues) in the HMW-MAA sequence 76-84. The first four amino acids of 76-84, LLQL, were similar to the first four amino acids from the VH (3-11) sequence. The change V→Q is neither a significant structural change nor a change in charge but results in a change in polarity. The last five amino acids, YSGRL, are similar with the last four amino acids of VH (3-11) sequence, YSKL, with the differences that $Tyr^5$ replaces $Leu^5$, and Gly is intercalated between $Ser^7$ and $Arg^8$. The HMW-MAA (76-84) peptide has lower binding affinity to HLA-A2 Ag than VH (3-11) peptide (Table 3). It also appears to be less protected from proteasome destruction than VH (3-11) peptide. On the basis of the nucleotide sequence, the $Leu^5 \rightarrow Tyr^5$ change is not the result of a point mutation but rather of the deletion of the base triplet encoding Leu. Thus, the position of the group $Tyr^6 Ser^7$ in VH (3-10) was shifted to $Tyr^5 Ser^6$ in HMW-MAA. Tyr and Ser should enhance Ag binding to TCR, because both contain free OH groups, which are most likely to form H bonds with the TCR. $Gly^7$ is intercalated before the COOH-terminal groups $Arg^8 Leu^9$ in HMW-MAA and $Lys^8 Leu^9$ in VH (3-11), respectively. On the basis of the nucleotide sequence, the change Lys→Arg is the result of a point mutation.

Because the shift of Tyr-Ser group may affect TCR recognition and Ag immunogenicity, Gly, which lacks side chain and allows flexible positioning, was introduced at position 5 of HMW-MAA (7684) to align the Tyr and Ser in both VH (3-11) and HMW-MAA peptides. The resulting sequence was LLQLGYSGRL. In this decapeptide, the amino acid positions 1, 2, 4, 6, and 7, and the COOH-terminal amino acids 9 and 10 are aligned with VH (3-11) peptide. Because this decapeptide contains the same COOH-terminal anchors as the nonapeptide LLQLYSGRL, the same TCR is likely to interact with both peptides, although with different affinities. VH3-11 and variant HMW-MAA (vHMW) peptides have the identical amino acids at positions 6 and 7. Their homology is seven of nine residues (77%). The binding affinities to HLA-A2 Ag of both wild-type (wt) and variant (v) HMW-MAA peptides are similar. The corresponding peptides were designated as I-100, VH: LLVLLYSKL; as I-101, wtHMW-MAA: LLQLYSGRL; and as I-102, vHMW-MAA: LLQLGYSGRL (Table 1).

EXAMPLE 2

This Example demonstrates the use of the peptides of the invention to stimulate increased CTL proliferative pesponses to both VH3-11 (1-100) and vHMW-MAA (1-102) peptides of lymphocytes from patients immunized with MELIMNE, a combination of the murine anti-idiotypic monoclonal antibodies MEL-2 and MF11-30 Pride et al., Clin Cancer Res 1998;4:2363).

Peptide I-100 (LLVLLYSKL) is from the anti-id mAb MF11-30 $VH_H$ residues 3-11. Peptide I-101 (LLQLYSGRL) corresponds to the wild-type amino acid sequence of HMW-MAA residues 76-84. Peptide I-102 (LLQLGYSGRL) has the amino acid sequence of the HMW-MAA stretch 76-84 modified by inclusion of Gly at position 80. Peptide F119 (AAGIGILTV) (SEQ ID NO:26) corresponds to the CTL epitope from MAA MART-1 (amino acids 27-35). Peptide E71, HER-2 (828-836) corresponds to an inactive HLA-A2 epitope from HER-2/neu protein. All of the peptides were synthesized in the M.D. Anderson Cancer Center Peptide Core Laboratory and purified by high-performance liquid chromatography. Their identity was determined by amino acid analysis. The purity of these peptides was >95%.

We tested first whether patients immunized with MELIMMUNE had T cells that recognized peptides from the anti-id mAb used as an immunogen as well as from the HMW-MAA. Of the 10 studied patients, 5 were free of disease 5-7 years after vaccination with MELIMMUNE, and 5 were being followed in the melanoma outpatient clinic at M.D. Anderson Cancer Center. All of the patients had disease resected a minimum of 2 months before study and had an Eastern Cooperative Oncology Group performance status of 0. None were currently receiving and/or had received chemotherapy and/or biological therapy within 2 months from study.

We determined whether PBMCs isolated from immunized patients responded to peptides I-100 and I-101 better than PBMCs from nonimmunized patients. In addition, we tested whether PBMCs contained T cells that recognized wtHMW-MAA and vHMW-MAA peptides.

For proliferation assays, PBMCs were cultured in tetra-triplicate in 96-well flat-bottomed microtiter plates (Costar Corp., Cambridge, Mass.) at the concentration of $2 \times 10^5$ cells/well in 100 μl of complete RPMI 1640 containing L-glutamine and 10% fetal bovine serum. Peptides I-100 and I-101 were added at 5, 25, and 50 μg/ml in serum-free RPMI 1640 up to a total volume of 200 μl. PBMCs were cultured for 6 days at 37° C. in a 5% $CO_2$ atmosphere before addition of tritiated thymidine at a concentration of 1 μCi/well. Results are expressed as cpm of tritiated thymidine incorporated and as a stimulation index (Hogan et al. J Immunol 1989; 142:2097-104). The latter is the average cpm of lymphocytes cultured with peptide divided by the average cpm of lymphocytes cultured without peptide. A proliferative response was scored as positive when mean cpm±SD values for cultures that were incubated with peptides differed significantly from those for cultures that were incubated without peptides ($P<0.05$, Student's t test). Peptide-specific T cells were propagated by adding recombinant interleukin $(IL)_2$ (90 IU/ml; Biosource International, Camarillo, Calif.) to PBMCs that had been cultured for 96 h at 37° C. with peptides. After 5 additional days of culture at 37° C. cells were washed, replated, and restimulated at a 1:1 stimulator to responder ratio with irradiated (30 Gy) autologous PBMC stimulators and peptides at concentrations of 5, 25, and 50 μg/ml. IL-2 was added after 96 h, and cells were cultured for an additional 5 days at 37° C., after which they were restimulated for an additional 10 days at 37° C. Lymphocytes stimulated over three cycles were collected and used as effectors in a cytotoxicity (CTL) assay.

In preliminary experiments we observed that peptide I-101 did not stimulate the proliferation or IFN-γ and IL-10 secretion by PBMCs from HLA-A2+ patient 6 and from four HLA-A2− patients, because these parameters were similar to those found in cultures of autologous PBMCs incubated without peptide. At restimulation with peptide I-101, the PBMCs of patient 6 became apoptotic, suggesting that the wtHMW-MAA was tolerogenic by deletional mechanisms (data not shown). Therefore, we focused our subsequent investigations on the analysis of VH3-11 (I-100) and vHMW-MAA (I-102) peptides, which appeared to be stimulatory.

As shown in Table 2, when incubated with I-100 and I-102 peptides for up to 6 days (1° stimulation; STIM), PBMCS from patients 1, 2, 4, and 6 proliferated to a markedly higher extent than autologous PBMCS incubated with no peptide (NP). The extent of proliferation induced by I-100 and I-102 peptides was similar. For Table 2, PBMC is peripheral blood mononuclear cells; NP is no peptide; S.I., stimulation index (values >2 are considered significant); a, $P<0.001$; b, $P<0.01$; c, significant increase over no peptide (NP); d, $P<0.05$. d

TABLE 2

| Patient no. | HLA-A2 phenotype/immunization | NP | I-100 | (S.I.) | I-102 | (S.I.) |
|---|---|---|---|---|---|---|
| 1 | +/+ | 456 ± 62 | 1123 ± 240[a] | (2.5) | 1519 ± 92[a] | (3.3) |
| 2 | +/+ | 256 ± 63 | 853[b,c] ± 138 | (3.3) | 766[b] ± 90 | (3.0) |
| 3 | − | 586 ± 47 | 655 ± 51 | (1.1) | 821[b] ± 45 | (1.4) |
| 4 | +/− | 380 ± 30 | 583[d] ± 97 | (1.5) | 640[b] ± 62 | (1.7) |
| 5 | − | 373 ± 55 | 630[a] ± 37 | (1.7) | 745[a] ± 61 | (2.0) |
| 6 | +/+ | 518 ± 32 | 1793 ± 58[a] | (3.1) | 1464 ± 53[a] | (2.8) |
| 7 | −/+ | 618 ± 58 | 652 ± 77 | (1.1) | 755 ± 56 | (1.2) |
| 8 | −/+ | 560 ± 22 | 490 ± 54 | (0.9) | 650 ± 31 | (1.2) |
| 9 | −/− | 455 ± 39 | 334 ± 26 | (0.7) | 425 ± 40 | (0.9) |
| 10 | −/− | 205 ± 13.7 | 184 ± 12 | (0.9) | 200 ± 20 | (1.0 |

Lymphocytes from the HLA-A2$^+$ patients 1, 2, and 6 who had been immunized with MELIMMUNE (Table 4) responded with significantly stronger proliferation to both I-100 and I-102 peptides and had significantly higher stimulation index (2.7±0.7) than HLA-A2$^-$ patients 3, 5, 9, and 10 who had not been immunized (1.2±0.4; P<0.001). Thus, induction of proliferation by I-100 and I-102 peptides was associated with HLA-A2 Ag expression and at a greater level than a peptide having the antigen sequence (I-101). These results also indicate that immunization activated a large population of T cells capable of responding to both VH3-11 (I-100) and vHMW-MAA (I-102) peptides. The mitogenic effect of VH3-11 and vHMW-MAA peptides was specific, because irrelevant HER-2/neu-specific peptide, E71, was not mitogenic for lymphocytes from HLA-A2$^+$ immunized patients 1,2, and 6 (NP=353±84 cpm versus E71=411±190 cpm; P=0.65) and HLA-A 2$^-$ patient 8 (NP=560±22 versus E71=685±103; P=0.06). Like the E71 peptide, the MART-1 peptide F119 was not mitogenic for PBMCs from patients 1 (330±36 cpm; stimulation index=0.7) and 10 (215±26 cpm; stimulation index=1.1).

EXAMPLE 3

This Example demonstrates cytokine induction by VH3-11 (I-100) and vHMW-MAA (I-102) peptides in PBMCs from immunized patients. Interaction of T cells with Ag can induce a few cycles of division resulting in Ag-primed uncommitted T cells or can induce T cells to differentiate and gain effector function. The effector function is best characterized by the ability of Ag-stimulated T cells to secrete Th1 cytokines and to mediate lysis of specific targets. To determine whether T cells from immunized patients acquired cytokine effector function, IFN-γ and IL-10 were measured in supernatants harvested from PBMC cultures stimulated with I-100 and I-102 peptides. To measure cytokine release, supernatants were collected at 24, 48, and 72 h after primary and secondary stimulation with 5, 25, and 50 μg/ml of peptides and stored frozen at −20° C. IFN-γ and IL-10 levels were measured by a double sandwich ELISA using the corresponding kits supplied by Biosource International. Assays were calibrated with human recombinant IFN-γ and IL-10 to detect each cytokine in a range of 15-1000 pg/ml.

IL-10 was assayed instead of IL-4 as a representative Th2 cytokine, because the PBMCs used as responders were from patients with melanoma. Therefore, they might contain regulatory cells. Patient 6 had supernatants saved from two separate experiments. This afforded validation of conclusions in replicated analyses performed at separated time points. Because after priming, all of the stimulated PBMCs were expanded in IL-2, we determined the effect of culturing PBMCs in IL-2 on IFN-γ induction. Representative individual patient examples of IFN-γ and IL-10 induction are shown in FIG. 3. Both IFN-γ and IL-10 levels from peptide-stimulated PBMCs from HLA-A2$^+$ patient 6 and HLA-A2$^-$ patient 7 were low after 1° STIM with peptide I-100 (FIGS. 3A and 3B).

To verify the significance of cytokine levels induced by I-100 and I-102 peptides, the cytokine responses induced by the dominant MART-1 epitope, represented by peptide F119, were determined in parallel. IFN-γ levels produced by PBMCs from HLA-A2$^+$ patient 6 stimulated with each of the peptides I-100, I-102, and F119 were similar (P>0.05; FIG. 3C). IL-10 levels after restimulation with control F119 peptide were significantly lower than those obtained with peptide I-102 (F119=58±11 pg/ml versus I-102=212±24 pg/ml; P<0.025) but were not significantly different from those obtained with peptide I-100 (86±11 pg/ml; P>0.05; FIG. 3D.).

IFN-γ and IL-10 responses from all of the patient PBMCs are shown in FIG. 4. Peak responses varied from patient to patient but, as a rule, responses were highest when measured after a 48- or a 72-h incubation with peptide (25 μg/ml). Cytokine secretion by PBMC from patients 8 and 9 could not be tested because additional lymphocytes could not be obtained from these two patients. After in vitro stimulation, there were no significant differences in mean pg/ml of IFN-γ±SD secreted after stimulation with I-100 peptide versus stimulation with I-102 peptide (FIG. 4A). The IFN-γ:IL-10 ratios at priming with both peptides were <1.0, although they were lower with I-100 peptide than with I-102 peptide. The IFN-γ:IL-10 ratios changed at restimulation to >3.0. IFN-γ levels were significantly (P<0.05) higher after 2° STIM than after 1° STIM, whereas IL-10 levels did not differ (FIG. 4B). After restimulation, IFN-γ levels in patients 2 and 6 increased by >1 log. The average IFN-γ levels after 2° STIM were significantly higher (616.1±86.3) for PBMCs from HLA-A2$^+$ patients than those for PBMCs from HLA-A2-patients (59.5÷24.4; P<0.007; FIG. 4C). A similar analysis for IL-10 did not detect significant differences (pg/ml IL-10: HLA-A2$^+$=155.7±36.3 versus HLA-A2$^-$=61.1±25; P=0.06). The IFN-γ:IL-10 ratios for HLA-A2$^+$ patients were 4-fold higher (3.96) than those for HLA-A2$^-$ patients (0.97) indicating a trend toward Th1 responses in HLA-A2$^+$ patients. Therefore, immunization with anti-id mAb MF11-30 recruited and activated T cells to acquire the potential of IFN-γ production. Demonstration of activation of effector cytokines required either priming and restimulation in vitro with peptide or culture of PBMCs in IL-2 before stimulation with peptide. Thus, the peptides of the invention can stimulate cytokine production in response to a particular antigen.

EXAMPLE 4

This Example demonstrates the induction of VH3-11 and vHMW-MAA peptide-specific CTLs by immunization with MELIMMUNE, followed by pulsing the CTLs with peptides of the invention. To determine the effects of the immunization with MELIMMUNE on activation of melanoma cell-lytic CTLs, we compared the responses of immunized HLA-A2+ patients 1 and 6 with that of nonimmunized HLA-A2+ patient 4. As specificity and restriction control we analyzed the responses of nonimmunized HLA-A2− patients 3 and 5. All of the CTLs were tested for their ability to lyse T2 cells pulsed with the stimulating peptide and A375sm melanoma cells. Lymphocytes collected after three rounds of peptide stimulation were tested for their ability to lyse $^{51}$Cr-labeled targets as described previously (Fisk, et al. J Exp Med 1998;181:2109-17; Murray, et al. Clin Cancer Res 2002;11:3407-18). To prove HLA-A2 restriction in CTL recognition, targets were incubated with 50 µg/ml of anti-HLA-A2 mAb MA-2.1. Cold target inhibition of tumor cell lysis experiments was performed as described (Murray, et al. Clin Cancer Res 2002;11:3407-18).

I-100-CTL and I-102-CTL from the HLA-A2+ patients 1 and 6 lysed I-100 pulsed T2 cells (T2-I-100) to a significantly greater extent than control targets T2-NP, i.e., T2 cells that had not been pulsed with peptide (FIGS. 5, A and B). CTLs induced by the HMW-MAA peptide I-102 also recognized the VH (3-11) peptide I-100 (data not shown). The HLA-A2+ patient 4 I-100-CTL did not lyse T2-I-100, yet autologous I-102-CTL lysed T2-I-102 (FIG. 5C). These results indicate that immunization with MELIMMUNE activated CTL precursors to both the VH3-11 peptide and to the HMW-MAA peptide, whereas in vitro stimulation with the same peptides of HLA-A2+ PBMCs from the nonimmunized patient activated only the existent CTL precursors for HMW-MAA. PBMCs from the HLA-A2− patients 3 and 5 that had not been immunized with MELIMMUNE but were only stimulated in vitro with VH3-11 and HMW-MAA peptides did not develop CTLs recognizing the stimulating peptide. As shown in FIGS. 5, D and E, there was no specific lysis of T2-I-102 targets by CTL from patient 3 stimulated repetitively with I-102 peptide compared with targets incubated without peptide (T2-NP). Lymphocytes from patient 5 were also unable to specifically lyse T2-I-100 and T2-I-102 targets (FIG. 5E). This indicates that CTL activation by I-100 and I-102 peptides is restricted by the HLA-2 binding motifs.

EXAMPLE 5

This Example demonstrates the induction of HMW-MAA-specific CTLs by immunization with MELIMMUNE and pulsing the CTLs with the peptides of the invention. To determine whether in vitro stimulation with peptides generated CTLs that recognized epitopes on HMW-MAA+/HLA-A2+ melanoma cells, PBMCs from immunized HLA-A2+ patients 1 and 6 were stimulated with I-100 and 1-102 peptides and then tested for their ability to lyse A375SM melanoma cells. As shown in FIG. 6A, the I-100-stimulated PBMCs and I-102-stimulated PBMCs of patient 1 effectively lysed A375SM cells, demonstrating that CTLs were present in peptide-stimulated PBMCs. Therefore, these effectors were designated as I-100 CTL and I-102 CTL, respectively. Lysis was effectively blocked by "cold" T2-I-100. This result demonstrated both the specificity of CTLs for the VH3-11 peptide and expression of a structurally similar peptide-HLA-A2 epitope on melanoma cells.

The results confirmed that the significant degree of homology in the sequence of epitopes formed by I-100 and I-102 peptides (>67%) resulted in CTLs cross-recognizing the HMW-MAA epitope presented by tumor cells. In addition, lysis was inhibited by HLA-A2-specific mAb MA2.1 by >50%, confirming that this molecule is the restricting element for CTL (FIG. 6B). Similar results were obtained with CTLs from patient 6. FIG. 6C shows the kinetics of lysis of A375SM cells by I-100-CTL and I-102-CTL. Effectors used as controls were generated from autologous PBMCs by stimulation in the same experiment and under the same experimental conditions with T2 cells, which had been pulsed with HMW-MAA peptide or incubated with IL-2 as a growth factor. The latter were designated as NP-CTL. NP-CTLs were used as effectors to determine whether memory CTLs induced by the vaccine were present in this patient and up-regulated their cytolytic function after stimulation with cytokines and HLA-A2 Ag, which was not presenting cognate Ag. The results show that NP-CTLs ("memory-like") specifically recognized an epitope on tumor cells, which is structurally similar to the one formed by T2-I-100. However, their lytic activity was weak and did not increase over time. In contrast, I-100-CTL recognized the same epitope with faster kinetics in the first 5 h than I-102-CTL. Their kinetics of lysis slowed over time. I-102-CTL recognized the same epitope on tumor cells with apparently slower kinetics than I-100-CTL, during the first 5 h, but the kinetics of lysis became somewhat faster over time compared with that of I-100-CTL (59% increase from 5 h to 20 h). We could not determine the exact number of effectors in each population bearing specific TCRs for each peptide, because the necessary reagents were not available. Nevertheless, the differences in kinetics of lysis between I-100-CTL and I-102-CTL suggest small quantitative differences in their functional avidity for tumor cells. Thus, the peptides of the invention can activate antigen specific CTLs.

EXAMPLE 6

To determine if the presence of short sequences within Ab2 showing homology to antigen epitopes and containing HLA binding sites was a more global phenomenon, other Ab2 were analyzed. We investigated four published amino acid sequences of Ab2/antiidiotypic antibody associated with human tumor antigen with known amino acid sequences. Two Ab2 have been generated and sequenced by one of us, and they bear the internal image of distinct determinants of human high molecular weight melanoma-associated antigen (HMW-MAA), which is expressed in a high percentage of melanoma lesions (Campoli M, et al. Crit Rev Immunol 2004;24:267-96.). These Ab2 are designated as MF11-30 and MK2-23, respectively (Kusama M, J Immunol 1989;143:3844-52.). The third Ab2, designated 105AD7, bears the internal image of CD55 antigen. CD55 is widely expressed by colorectal carcinoma cells (Medof M E, Proc Natl Acad Sci U S A 1987;84: 2007-11. Spendlove L, et al. Eur J Immunol 2000;30:2944-53.) The fourth Ab2, designated 3H1, bears the internal image of carcinoembryonic antigen (Potter, et al. Mol Immunol 1998;35:1179-87; Beauchemin et al. Mol Cell Biol 1987;7:3221-30.).

In order to identify homology between these Ab2 and their respective antigens, we searched for unique $V_H$ peptides preceding FR1. Then, utilizing proteomics programs available at http://bimas.dcrt.nih.gov/molbio/hla_bind, we searched for HLA-A2 binding motifs in the unique $V_H$ peptides we had identified.

To identify homologous amino acid sequences in the tumor antigen, the sequences of the identified unique VH peptides containing HLA-A2 binding motifs were compared with the amino acid sequences of the corresponding tumor antigen (HMW-MAA, CD55, and CEA). Peptides from Ab2 CDR3, which lacked or showed minimal homology with other immunoglobulin amino acid sequences, were analyzed in parallel. We found that two of the four Ab2 (mAb MF11-30 and 105AD7) contain unique amino acid sequences located before FR1. FR1 starts with a distinctive motif: EVQ, QVQ, EDQ in position 17 to 19. These unique $V_H$ peptides encompass the first 18 and 24 amino acids of mAb MF11-30 and 105AD7 $V_H$, respectively, as depicted in FIG. 1. The other two Ab2 (mAb MK2-23 and 3H1) do not contain unique $V_H$ peptides preceding FR1. The unique $V_H$ peptides with HLA-A2 binding motifs from mAb 105AD7 and MF11-30 are shown in Table 3. Candidate CTL epitopes are shown in bold. The mAb 105AD7 amino acid sequence after amino acid 18 is added to show the complete amino acid sequence of the second CTL epitope. The Table 3 sequence from mAb MF11-30 is provided as SEQ ID NO:1; the sequence from mAb 105AD7 is provided as SEQ ID NO:2.

acid sequence in CDR3 shows poor homology with other $V_H$ amino acid sequences. It should be noted that the $V_H$ CDR3 (100-117) amino acid sequence is 50% homologous with HMW-MAA (690-706) amino acid sequence. The CDR3 amino acid sequence resembles an MHC class II epitope due to the presence of hydrophobic aliphatic and aromatic amino acids, which are known to form MHC class II anchors. Peptides with this sequence may activate $CD4^+$ T cells as reported for CDR3 peptides from mAb 3H1. Surprisingly, we found significant homology between the $NH_2$-terminal $V_H$ 3H1 peptide (12-20) and CEA isoform 1 (100-108). The

TABLE 3 mAb MF11-30 $^1$K M L L V L L Y S K L S S Q C A E D Q T A V H L$^{24}$ mAb 105AD7 $^1$D T L C Y T L L L T I P S R V L S$^{18}$-Q V T L

Amino acid sequence homology (labeled "H" in Table 4) between $V_H$ of Ab2 and tumor antigens HMW-MAA, CD55, and CEA is shown in Table 4. The amino acid sequence similarity was determined using the Expasy SIM alignment program. Identical or very similar residues are shown in bold. Substituted and inserted residues in Ab2 are enlarged. Also, the HLA allospecificity bound by both Ab2 and tumor antigen peptide is indicated. The HLA allospecificity bound with the highest affinity is underlined. Determinations of allospecificity were made using the HLA peptide motif search program BIMAS.

By convention, the designation "105AD7(7-16)" indicates a peptide sequence having a start position ("SP") of amino acid number 7 of the VH and which includes amino acids 7-16. Two of mAb 105AD7 peptides, designated as 105AD7 (7-16) and 105AD7 (2-10), showed significant homology, 6/10 (60%) and 5/9 (55%), respectively, with CD55 (14-23) and CD55 (373-381) amino acid sequences, as shown in Table 2. For this Table "SI" designates the SEQ ID NO for each of the amino acid sequences. The characterization for the Ab2 antigen pair HMW-MAA and mAb MF11-30 are provided in Example 1.

two nonamers, 3H1 (12-20) and CEA-1(100-108), are 55% homologous and can bind to HLA class I antigens. Based on alignment with the IMGT program (imgt.cines.fr), the VH of mAb MF11-30 and 105AD7 belong to VH families Q52 and IgG VHII, respectively. The first 23 amino acids of mAb MF11-30 VH are absent from all other IgGs analyzed. The first six NH2-terminal amino acids of mAb 105-AD7 VH are absent from most IgGs. Compared with the few more homologous IgG or hypothetical proteins, the following 11 amino acids had one deletion, which resulted in a misalignment plus at least four to five nonconservative changes.

The homology between tumor antigen and Ab2 amino acid sequences is not random. It was not observed with amino acid sequences from the immunoglobulin light chain. Also, $V_H$ of human myelomas which contain unique FR1 (Trojan et al. Nat Med 2000;6:667-72) did not show such extensive homology with HMW-MAA and CD55 as the one reported here (data not shown).

Therefore, to summarize, two of the Ab2 analyzed in this Example carry unique $NH_2$-terminal $V_H$ sequences whereas

TABLE 4

| Ab2 Pair Allospecificity | SP | Sequence | SI | (H) | HLA |
|---|---|---|---|---|---|
| 1 MF11-30 | 3 | L L V L L Y S K L | 3 | 5/9 | A201, A205, A24, B2705 |
| HMW-MAA | 74 | L L Q L Y S G R L | 4 | | |
| 2 MF11-30 | 16 | A E D Q T A V H L | 5 | 5/9 | B60, B61, B2705, B4403 |
| HMW-MAA | 303 | V E D T F C F H V | 6 | | |
| 3 105AD7 | 2 | T L C Y T L L L T | 7 | 5/9 | A201, B2705 |
| CD55 | 373 | T L V T M G L L T | 8 | | |
| 4 105AD7 | 7 | L L L T I P S R V L | 9 | 6/10 | A201, B62, B2705, B5102 |
| CD55 | 14 | L L G E L P R L L L | 10 | | |
| 5 105AD7 | 14 | R V L S Q V T L | 11 | 6/8 | A201, A205, B2705 |
| CD55 | 20 | R L L L L V L L | 12 | | |
| 6 MK2-23 | 12 | V Q P G G S R K L | 13 | 5/9 | A24, B7, B2705 |
| HMW-MAA | 1,020 | V A R G G R R L L | 14 | | |
| 7 MK2-23 | 37 | V R Q A P E K K G L | 15 | 6/10 | A205, A24, B2705, B3902 |
| HMW-MAA | 825 | V V Q A P R K G N L | 16 | | |
| 8 3H1 | 12 | E L V K P G A S L | 17 | 5/9 | A24, B14, B62, B3901 |
| CEA | 100 | E T I Y P N A S L | 18 | | | mAb MK2-23 and 3H1 do not express unique $NH_2$-terminal $V_H$ amino acid sequences. However, two mAb MK2-23 peptides, MK2-23(12-20) and MK2-23(37-46), show significant homology with HMW-MAA (1020-1028) and (825-834) amino acid sequences. mAb MK2-23 amino two Ab2 do not. All four $NH_2$-terminal $V_H$ are more than 50% homologous with the inducer tumor antigen. We have designated these Ab2/antiidiotypic antibody $NH_2$-terminal $V_H$ sequences as T-cell idiotopes because they are homologous with somatic antigen.

The major structural differences between the tumor antigen peptides and the corresponding T-cell idiotopes include (a) introduction or removal of charged residues; (b) insertion of groups which lead to misalignments; and (c) introduction of polar residues which form H-bonds. Of the eight pairs of Ab2-tumor antigen shown in Table 2, changes in charged residues are present in the pairs mAb 105AD7 (7-16)/CD55 (14-23), mAb MK2-23 (37-46)/HMW-MAA (825-834), and mAb 3H1 (12-20)/CEA (100-108). Misalignments are generated by insertion of (a) $Ser^7$ in mAb 105AD7 (7-16), which shifts the almost identical group (RVL) with the CD55 (14-23) group: RLL; (b) $Ser^6$ in mAb MD2-23, which also shifts the almost identical group: RKL with the HMW-MAA group RRL; and (c) $Asp^6$ in mAb MK2-23, which also shifts the almost identical group KKG with the group RKG in HMW-MAA (825-833). The Ab2-tumor antigen peptide pairs which lack changes in charged residues show changes in polar residues such as $Ser^7 \rightarrow Gly^7$ (pair 1), $Thr^5 \rightarrow Phe^5$ (pair 2), as well as $Cys^3 \rightarrow Val^3$ (pair 3).

Thus, the method of identifying T cell epitopes disclosed herein differs from previous methods mechanism for generation of candidate CTL by identifying the sequence of the CTL epitope of the tumor antigen nested in Ab2 and identifying HLA binding motifs therein. Accordingly, Ab2 peptides homologous with tumor antigen peptides and which comprise HLA binding motifs are stronger immunogens for induction of CTL recognizing tumors expressing these antigens when compared to the tumor antigen peptides.

While this invention has been illustrated by specific embodiments, routine modifications will be apparent to those skilled in the art and such modifications are intended to be within the scope of the invention and the following claims.

The invention claimed is:

1. An isolated peptide selected from the group consisting of a peptide consisting of the seciuence Leu-Leu-Val-Leu-Leu-Tyr-Ser-Lys-Leu (SEQ ID NO: 23) and a peptide consisting of the sequence Leu-Leu-Gln-Leu-Gly-Tyr-Ser-Gly-Arg-Leu (SEQ ID NO:25).

2. A composition comprising one or both of the peptides of claim 1.

3. The composition of claim 2, further comprising a pharmaceutically acceptable carrier.

* * * * *